(12) United States Patent
Kim et al.

(10) Patent No.: US 7,764,815 B2
(45) Date of Patent: Jul. 27, 2010

(54) METHOD OF DIGITAL IMAGE ANALYSIS FOR ISOLATING A REGION OF INTEREST WITHIN A TONGUE IMAGE AND HEALTH MONITORING METHOD AND APPARATUS USING THE TONGUE IMAGE

(75) Inventors: Tae-woo Kim, Seongnam-si (KR); Gil-won Yoon, Seoul (KR); Jeong-whan Lee, Suwon-si (KR); Sang-hoon Shin, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 1547 days.

(21) Appl. No.: 10/746,257

(22) Filed: Dec. 29, 2003

(65) Prior Publication Data

US 2004/0151379 A1  Aug. 5, 2004

(30) Foreign Application Priority Data

Dec. 28, 2002  (KR) .................. 10-2002-0085915

(51) Int. Cl.
*G06K 9/00* (2006.01)
(52) U.S. Cl. ....................... 382/128; 382/209
(58) Field of Classification Search ................ 382/115, 382/128, 209; 600/590
See application file for complete search history.

(56) References Cited

U.S. PATENT DOCUMENTS 5,774,357 A * 6/1998 Hoffberg et al. ............ 713/600
5,872,859 A    2/1999 Gur et al.
6,363,160 B1 * 3/2002 Bradski et al. ............. 382/103
6,964,023 B2 * 11/2005 Maes et al. ................. 715/811
2003/0103682 A1 * 6/2003 Blake et al. ................ 382/282

FOREIGN PATENT DOCUMENTS

JP    07-000398    1/1995
JP    2001-314376  11/2001

(Continued)

OTHER PUBLICATIONS

Pang et al., On Automated Tongue Image Segmentation in Chinese Medicine, Aug. 11-15, 2002, 16th ICPR 2002, vol. 1, pp. 616-619.*

(Continued)

*Primary Examiner*—Matthew C Bella
*Assistant Examiner*—Dennis Rosario
(74) *Attorney, Agent, or Firm*—Cantor Colburn LLP

(57) ABSTRACT

A health monitoring method using a tongue image including constructing a database in which a tongue image obtained from a person, a template image set for the person, and a result of determining a health condition of the person with respect to at least one characteristic factor are linked together; isolating a region of interest within the tongue image, which is acquired from a person whose health condition is to be determined, using template matching; detecting at least one characteristic factor from the isolated region of interest; and determining a health condition of the person based on a change in an appearance of the tongue, which is detected by a comparison between the detected characteristic factor and a characteristic factor searched from the database with respect to the region of interest in different health conditions.

19 Claims, 11 Drawing Sheets

FOREIGN PATENT DOCUMENTS

JP    2003-310585    11/2003

OTHER PUBLICATIONS

Su et al., The Approach of Data Mining Methods for Medical Database, Engineering in Medicine and Biology Society, vol. 4, pp. 3824-3826.*

Wang et al., Pattern Recognition:From Classical to Modern Approaches: Chapter 21: Tongue Diagnosis Based on Biometric Pattern Recognition Technology, 2001, World Scientific Publishing Co. Pte. Ltd., pp. 594.*

Yao and Paotia, "Comparison of TCM Tongue Images with Gastroscopy Images", (in Chinese) Shandong S & T Publisher, 1996.

Cai, Yang, "A Novel Imaging System for Tongue Inspection", IEEE Instrumentation and Measurement, Technology Conference, Anchorage, AK, USA, pp. 159-163 (May 21-23, 2002).

Chiu, Chuang-Chien, "A novel approach based on computerized image analysis for traditional Chinese medical diagnosis of the tongue", Computer Methods and Programs in Biomedicine, 61, pp. 77-89, (2000).

Watsuji, Tadashi, et al, "Medical Application of fuzzy theory to the diagnostic system of tongue inspection in traditional Chinese medicine", 1999 IEEE International Fuzzy Systems Conference Proceedings, Seoul, Korea, pp. I-145-I-148, (Aug. 22-25, 1999).

Liu, Lei Jian, et al., "Efficient Segmentation of Nuclei in Different Color Spaces" SPIE, (Intnl. Society for Optical Engineering), vol. 2298, pp. 773-778 (Jul. 26, 1995) [XP-002360888].

Sento, Seishira, "Diagnostic significance of the tongue from the aspect of traditional oriental medicine: Diagnostics and therapeutics by obtaining a whole condition from local characteristics", Sento Clinic of Traditional Chinese Medicine, pp. 231-236 (including English Abstract) (Feb. 28, 2002).

* cited by examiner

METHOD OF DIGITAL IMAGE ANALYSIS FOR ISOLATING A REGION OF INTEREST WITHIN A TONGUE IMAGE AND HEALTH MONITORING METHOD AND APPARATUS USING THE TONGUE IMAGE

BACKGROUND OF THE INVENTION

1. Field of the Invention

The present invention relates to health monitoring. More particularly, the present invention relates to a method of digital image analysis for isolating a region of interest within a tongue image and a health monitoring method and apparatus using characteristic factors detected within the region of interest within the tongue image.

2. Description of the Related Art

With overall improvements in quality of life and living conditions, interest in personal health has increased. As a result, a significant amount of home medical equipment that allows people to easily monitor their personal health has been researched and developed.

Many factors may be used to diagnose a condition of a human body. Among them, blood pressure or blood glucose is usually used due to ease of measurement. In addition to these factors, it has been recently acknowledged that a condition of a tongue may also provide significant information about a condition of an internal organ. For example, a tongue of a healthy person is pink in color and has a thin, white tongue coat. When a person's liver or a digestive organ is not functioning properly, an appearance of that person's tongue may change. For example, that person's tongue may become swollen, thin, shrink due to dryness, have a yellow or gray color, have a thick tongue coat, or be slick without any tongue coat.

However, equipment for detecting an incipient stage of an invasion of a disease and progression of the disease based on a condition of the tongue, such as a tongue coat, color, or appearance, is very expensive and is typically only found in hospitals. As such, the conventional equipment is not suitable for people to personally monitor their health.

SUMMARY OF THE INVENTION

The present invention provides a method of digital image analysis for isolating a region of interest, such as a tip, middle part, edge, or root of a tongue, within a tongue image.

The present invention also provides a health monitoring method and apparatus using at least one characteristic factor of a region of interest isolated within a tongue image.

According to a feature of an embodiment of the present invention, there is provided a method of digital image analysis for isolating a region of interest within a tongue image including constructing a database in which a plurality of template images are stored, each template image corresponding to personal information and having regions of interest indicated thereon, acquiring the tongue image from a person whose health condition is to be determined, segmenting a tongue area within the tongue image acquired from the person whose health condition is to be determined, matching the tongue area with one of the plurality of template images stored in the database, and isolating a region of interest from the matched template image.

The method may further include compensating for color distortion of the tongue image by using a color checker before segmenting the tongue area. Compensating for color distortion may include generating and storing a color checker including a plurality of colors to be displayed on the tongue image during the acquisition of the tongue image, comparing the color checker included in the tongue image with a color checker provided from the tongue image acquisition unit, obtaining a color difference value between the two color checkers, and determining a degree of compensation based on the color difference value.

In the method, segmenting the tongue area may include performing thresholding on each pixel in the tongue image using a predetermined threshold value to define an inner mouth area and a tongue area and segmenting the tongue area within the tongue image. Thresholding may be performed using at least one among Red/Green/Blue (RGB) color values of each pixel in the tongue image or using an intensity (I) value obtained by converting RGB color values of each pixel in the tongue image into Hue Saturation Intensity (HSI) color values.

In the method, matching the tongue area may include calculating a tongue width, a rotation angle of a tongue, and a tongue length with respect to the segmented tongue area and matching the tongue image with the template image using the tongue width, the rotation angle, and the tongue length.

The region of interest may be at least one region of the tongue including a tongue middle, a tongue root, a tongue edge, and a tongue tip.

According to another feature of an embodiment of the present invention, there is provided a computer readable recording medium, including a first program for constructing a database in which template images are stored, each template image corresponding to personal information and having regions of interest indicated thereon recorded on the medium, a second program for performing thresholding using a predetermined threshold value on a tongue image, which is acquired from a person whose health condition is to be determined, to segment the tongue image into an inner mouth area and a tongue area recorded on the medium, a third program for matching the acquired tongue image with the template image using a tongue width, a rotation angle of the tongue, and a tongue length which are calculated from the tongue area recorded on the medium, and a fourth program for isolating a region of interest from the matched tongue image recorded on the medium.

According to yet another feature of an embodiment of the present invention, there is provided a health monitoring method using a tongue image including constructing a database in which a tongue image obtained from a person, a template image set for the person, and a result of determining a health condition of the person with respect to at least one characteristic factor are linked together, isolating a region of interest within the tongue image, which is acquired from a person whose health condition is to be determined, by using template matching, detecting at least one characteristic factor from the isolated region of interest, and determining the health condition of the person based on a change in an appearance of the tongue, which is detected by a comparison between the detected characteristic factor and a characteristic factor searched from the database with respect to the region of interest in different health conditions.

In the method, isolating the region of interest may include performing thresholding on each pixel in the acquired tongue image using a predetermined threshold value to segment the tongue area from the tongue image. The thresholding may be performed using at least one among Red/Green/Blue (RGB) color values of each pixel in the tongue image or using an intensity (I) value obtained by converting RGB color values of each pixel in the tongue image into Hue Saturation Intensity (HSI) color values.

The characteristic factor may be an average of H, S, or I values obtained from a histogram of an HSI color coordinate system for the region of interest.

The region of interest may be at least one region including a tongue middle, a tongue root, a tongue edge, and a tongue tip.

The method may further include informing the person of the result of determining the health condition via a wired connection or wirelessly.

According to yet another feature of an embodiment of the present invention, there is provided a computer readable recording medium including a first program for constructing a database in which a tongue image obtained from a person, a template image set for the person, and a result of determining a health condition of the person with respect to at least one characteristic factor are linked together recorded on the medium, a second program for isolating a region of interest from a tongue image, which is acquired from a person whose health condition is to be determined, using template matching recorded on the medium, a third program for detecting at least one characteristic factor from the isolated region of interest recorded on the medium, and a fourth program for determining the health condition of the person based on a change in an appearance of the tongue, which is detected by a comparison between the detected characteristic factor and a characteristic factor searched from the database with respect to the region of interest in different health conditions recorded on the medium.

According to still yet another feature of an embodiment of the present invention, there is provided a health monitoring apparatus using a tongue image including a tongue image database in which a tongue image obtained from a person, a template image set for the person, and a result of determining a health condition of the person with respect to at least one characteristic factor are linked together, a tongue image acquisition unit for acquiring the tongue image from a person whose health condition is to be determined, a region of interest isolator for segmenting a tongue area within the tongue image provided from the tongue image acquisition unit and for isolating a region of interest from the tongue area using template matching between the tongue area and a template image stored in the tongue image database, a characteristic detector for generating data regarding at least one characteristic factor with respect to the region of interest isolated by the region of interest isolator, a comparator for comparing the data regarding the characteristic factor generated with respect to the region of interest by the characteristic detector with a characteristic factor stored in the tongue image database with respect to the region of interest, and a health condition determiner for determining the health condition of the person based on the result of comparison provided from the comparator and for informing the person of the result of the determination.

The apparatus may further include a color compensator for compensating for color distortion of the tongue image acquired by the tongue image acquisition unit using a color checker and for providing the compensated tongue image to the region of interest isolator.

The region of interest isolator may perform template matching using a tongue width, a rotation angle of a tongue, and a tongue length, which are calculated from the tongue area.

The health monitoring apparatus may be integrated into a mobile communication equipment having a digital camera or into a personal computer having a digital camera.

The tongue image database, the region of interest isolator, the characteristic detector, the comparator, and the health condition determiner may be implemented in a remote health care service center, and the tongue image acquired by the tongue image acquisition unit may be transmitted via a wired connection or wirelessly to the health care service center. The health care service center may be a computer server of a mobile communication equipment company or a hospital.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
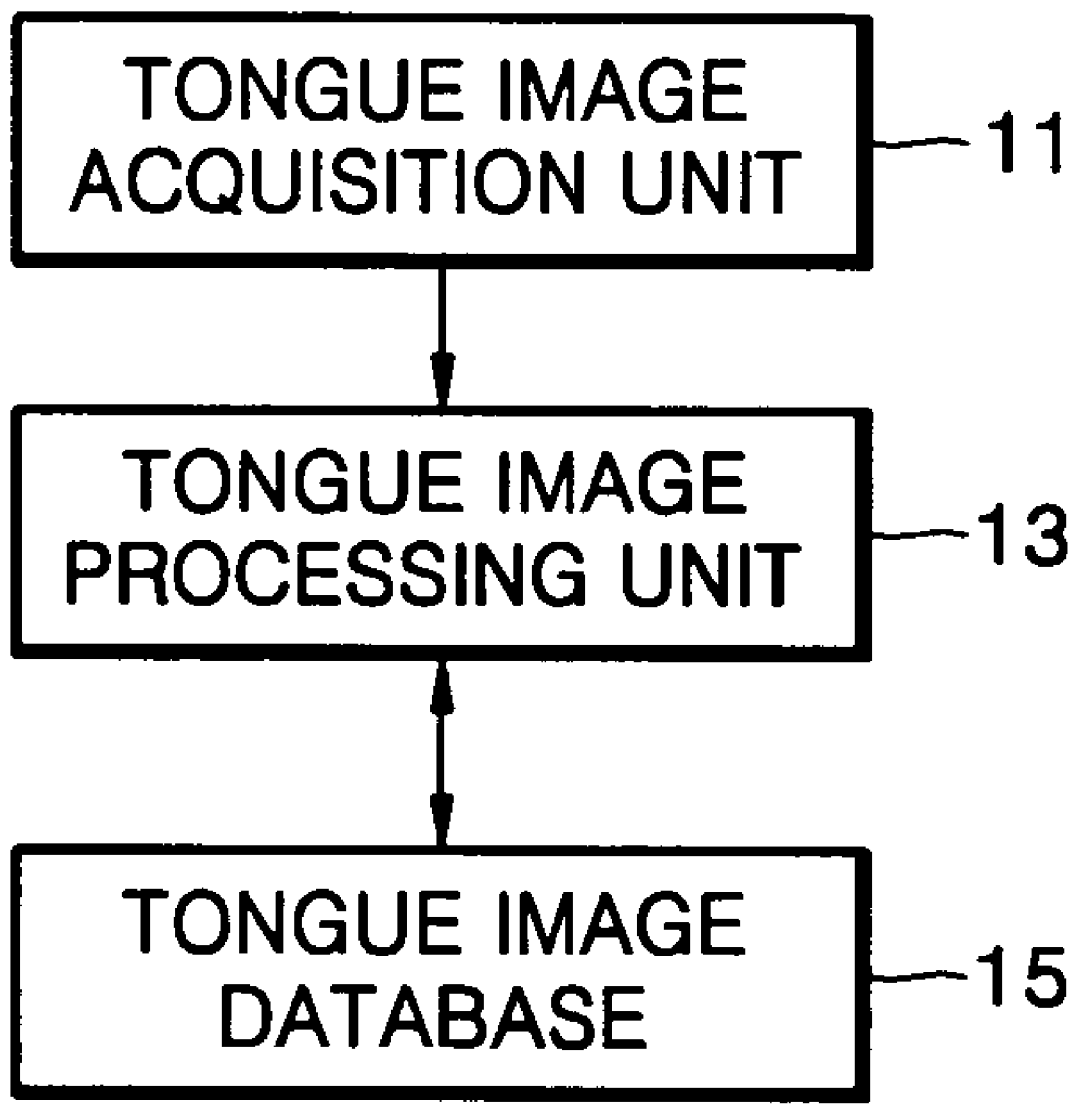
FIG. 1 is a block diagram of a health monitoring apparatus using a tongue image according to an embodiment of the present invention.

Korean Patent Application No. 2002-85915, filed on Dec. 28, 2002, and entitled: "Method of Isolating a Region of Interest Within a Tongue Image and Health Monitoring Method and Apparatus Using the Tongue Image," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. Like reference numerals refer to like elements throughout.

FIG. 1 is a block diagram of a health monitoring apparatus using a tongue image according to an embodiment of the present invention. The health monitoring apparatus includes a tongue image acquisition unit 11, a tongue image processing unit 13, and a tongue image database 15.

The tongue image acquisition unit 11 is implemented as a digital camera, such as a camera exclusively for photographing the tongue, a camera attached to a personal computer, or a camera attached to a mobile communication terminal. In a method according to the present invention, the tongue of a person to be diagnosed is photographed using the tongue image acquisition unit 11 every day, or as necessary, before food is consumed. The tongue image acquisition unit 11 acquires a tongue image and transmits it to the tongue image processing unit 13. Preferably, the tongue is photographed under constant illumination to reduce color distortion of a tongue image. In addition, it is preferable that the color of the tongue image is compensated using a color checker. To achieve best results, the person to be examined should extend the tongue in almost the same form, for example, to have almost the same length or make the same angle, every time the tongue is photographed.

The tongue image processing unit 13 isolates a region of interest, such as a tongue tip, a tongue middle, a tongue edge, or a tongue root, within the tongue image provided from the tongue image acquisition unit 11. The tongue image processing unit 13 isolates the region of interest using thresholding and template matching with a basic tongue image stored in the tongue image database 15, and then compares the region of interest isolated within the currently acquired tongue image with that in the basic tongue image based on predetermined characteristic factors. In addition, the tongue image processing unit 13 may compare a tongue itself or a coat of a tongue in the region of interest with the basic tongue image based on predetermined characteristic factors and determine a person's health condition based on principles of Chinese medicine.

The tongue image database 15 includes personal information including a unique identifier of each person, a tongue image acquired from each person by the tongue image acquisition unit 11, a template image in which regions of interest are set, and characteristic factor data with respect to each region of interest in each health condition or on each date, which are associated with one another.

In the health monitoring apparatus, the tongue image acquisition unit 11, the tongue image processing unit 13, and the tongue image database 15 may be integrated into a single apparatus or may be separately implemented. When the components are integrated into a single apparatus, the health monitoring apparatus may be implemented in a personal mobile communication equipment, such as a cellular phone or a personal digital assistant (PDA). In this case, the tongue image database 15 stores personal information, tongue information, and tongue characteristics, with respect to a tongue image of the owner of a mobile communication equipment. When the components are separately implemented, data transmission and reception is performed among the components using wired or wireless communication, and the tongue image processing unit 13 and the tongue image database 15 may be implemented in a health care service center or a personal computer. The health care service center may be a computer server of a mobile communication equipment company or a computer server of a hospital. In the meantime, only the tongue image database 15 may be separately implemented, and when necessary, a tongue image may be transmitted over wires or wirelessly from the tongue image database 15 to a remote medical doctor having training in principles of Chinese medicine, and that medical doctor may diagnose a health condition and give advice based on principles of Chinese medicine.

Figure 2:
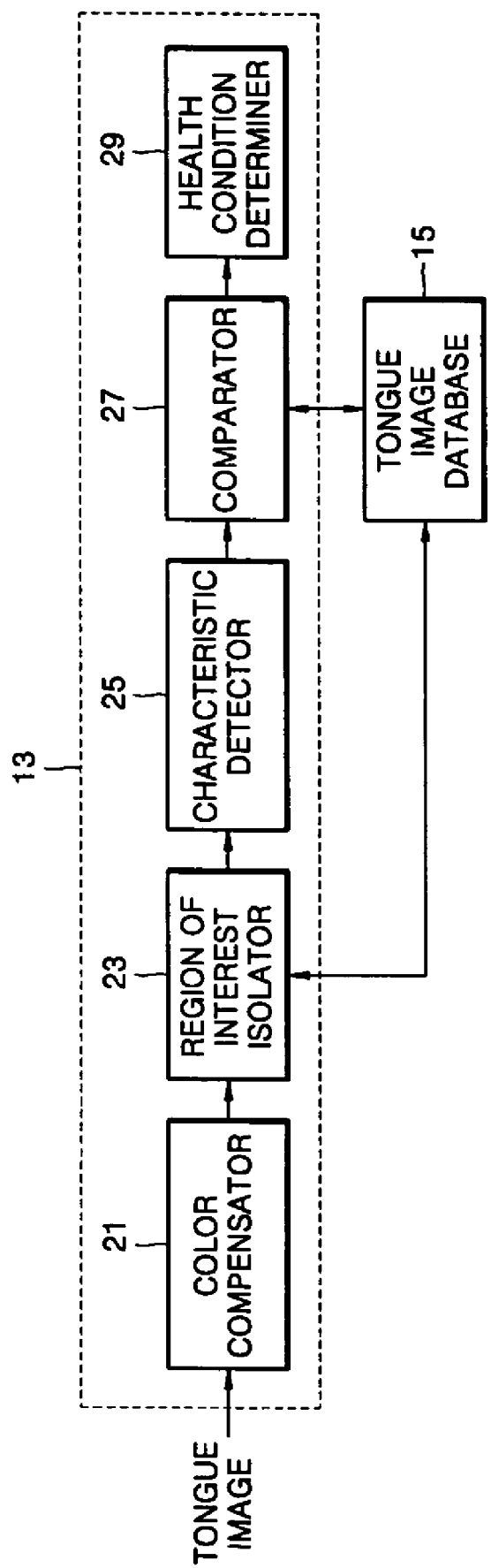
FIG. 2 is a detailed block diagram of a tongue image processing unit shown in FIG. 1.

FIG. 2 is a detailed block diagram of the tongue image processing unit 13 shown in FIG. 1. The tongue image processing unit 13 includes a color compensator 21, a region of interest isolator 23, a characteristic detector 25, a comparator 27, and a health condition determiner 29.

The color compensator 21 compensates a tongue image for a color distortion due to ambient illumination during acquisition of the tongue image using the tongue image acquisition unit 11. To perform color compensation, the tongue image acquisition unit 11 generates and stores a color checker including a plurality of colors to be displayed on the tongue image when acquiring the tongue image. Then, the color compensator 21 compares the color checker included in the tongue image with the color checker provided from the tongue image acquisition unit 11, obtains a color difference value between the two color checkers, and determines a degree of compensation based on the color difference value. In an alternate embodiment of the present invention, the color compensator 21 may be omitted. More specifically, the color compensator 21 is optional according to an environment in which the tongue is photographed.

The region of interest isolator 23 matches the tongue image received from the color compensator 21 with a basic template image of a relevant person, which is stored in the tongue image database 15, and isolates a region of interest, such as a tongue tip, a tongue middle, a tongue left edge, a tongue right edge, or a tongue root.

The characteristic detector 25 detects characteristic factors of the region of interest isolated by the region of interest isolator 23. The characteristic detector 25 may detect characteristic factors such as a histogram of color values in a Hue Saturation Intensity (HSI) color coordinate system, an average of the color values, a deviation, entropy, and texture.

The comparator 27 compares the characteristic factors of the region of interest of the tongue image, which are detected by the characteristic detector 25, with characteristic factors of the region of interest of the basic template image that are stored in the tongue image database 15 according to health conditions or dates.

The health condition determiner 29 has a data range for each characteristic factor with respect to a health condition, the range being set in advance, and determines the health condition of a current person using the result of the comparison provided from the comparator 27. For example, H, S, and I values obtained from an HSI histogram of a tongue tip, which are stored with respect to a healthy condition and a fatigue condition in the tongue image database 15, may be compared with H, S, and I values obtained from an HSI histogram of a tongue tip isolated within a currently acquired tongue image, and a current health condition may be determined based on the result of the comparison. In addition, appearances of the tongue itself and the coat of the tongue in the region of interest may be detected based on the result of comparison of characteristic factors to determine a current health condition based on principles of Chinese medicine.

Table 1 shows internal organs corresponding to each part of the tongue and health conditions based on principles of Chinese medicine.

TABLE 1

| Items | Description |
|---|---|
| Organs | Tongue tip: Upper heater, Upper part of the stomach - Heart and lungs<br>Tongue middle: Middle heater, Middle part of the stomach - Spleen and Stomach<br>Tongue edge: None - Liver and gallbladder<br>Tongue root: Lower heater, Lower part of the stomach - Kidney |
| Health criteria | Health condition is determined based on appearances of tongue itself and coat of tongue.<br>Tongue proper: Mainly determines a deficiency or an excess of organs. |

TABLE 1-continued

| Items | Description |
|---|---|
| | Tongue coat: Mainly determines the clarity or turbidity of the stomach "Gi" and properties of pathogen.<br>(Healthy condition: Tongue itself has a reddish and glossy appearance and a thin white coat; the tongue is neither too dry nor too damp.) |
| Tongue itself | White: White tongue itself indicates deficiency and cold syndrome or anemia.<br>Reddish: Reddish tongue tip indicates abundant heat in the upper heater or flaring-up of the heart fire. Reddish tongue edge indicates a hepatic heat syndrome. Scarlet tongue color indicates steaming fever due to a warm heart, i.e., a flaming up of fire due to deficiency of Eum. Crimson appears mostly when pathogenic heat enters the nutrient "Gi".<br>Purple: The three heaters have extreme heat. Dark blue indicates accumulation of stagnated blood. A damp tongue having a light purple color with blue indicates that a cold pathogen has entered the liver and kidneys.<br>Dark blue: Slippery tongue indicates deficiency of Eum. Dryness indicates the syndrome of blood stagnation. These two characteristics indicate that a disease has advanced. |
| Tongue coat | White coat: White, sticky, and slippery coat indicates that body contains damp phlegm. White, sticky, and thick coat indicates abundant damp turbidity. An appearance as if tongue was shaken in powder indicates that turbidity of epidemic disease is high. White coat is mostly exterior syndrome in exogenous diseases.<br>Yellow coat: A light yellow and non-dry coat indicates that a pathogen has started to enter the body. Yellow and sticky coat indicates damp heat. A yellow and stained like coat indicates that damp is more vigorous than heat. A dark yellow and cracked coat indicates that heat is more vigorous than damp.<br>Dark gray coat: A gray, lightly moistened and slippery coat with light viscosity and stagnation indicates Eum-cold due to accumulation of fluids or direct attack of an exogenous pathogenic factor. A dry and dark coat indicates that abundant heat damages a thin body fluid and extreme fire dries up water. A moistened and slippery coat indicates deficiency of Yang and excessive Eum, that is, a dominance of water over fire. |

Figure 3:
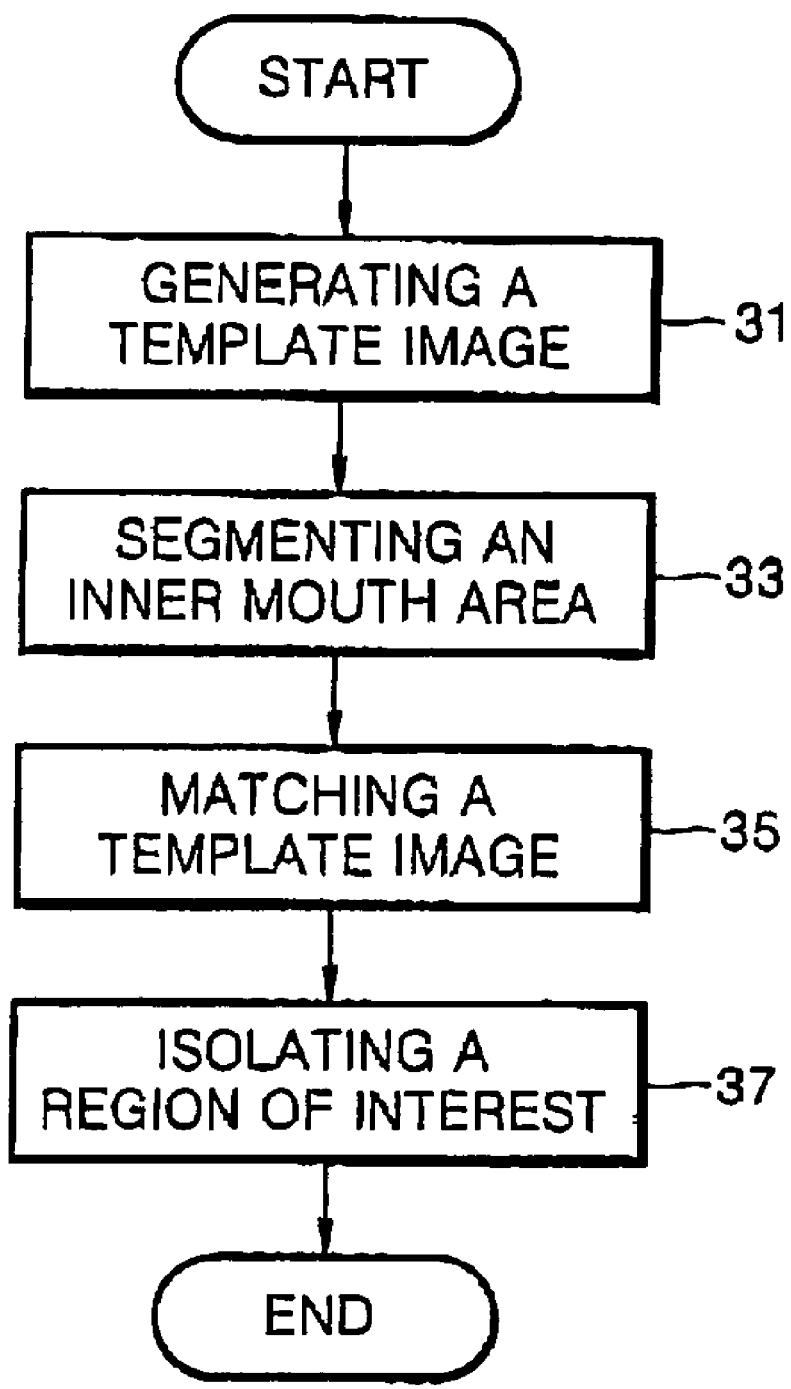
FIG. 3 is a flowchart of an operation of a region of interest isolator shown in FIG. 2.

FIG. 3 is a flowchart of an operation of the region of interest isolator 23 shown in FIG. 2. The operation includes generating a template image in step 31, segmenting an inner mouth area in step 33, matching a template image in step 35, and isolating a region of interest in step 37.

In step 31, a template image of the tongue of a person is generated and stored in the tongue image database 15. Step 31 will be described in detail with reference to FIGS. 4A through 4D.

Figure 4A:
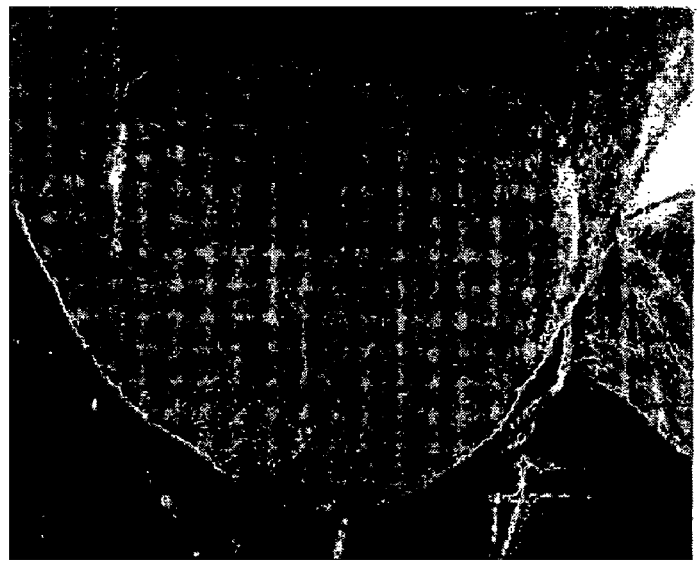
FIGS. 4A through 4D illustrate a generation and matching of a template image stored in a tongue image database.

In order to generate a template image of the tongue, thresholding is performed on a tongue image acquired by the tongue image acquisition unit 11 to segment the tongue image into an inner mouth area, which roughly occupies ¼ of the image above the tongue, and a tongue area. Thresholding of the tongue image shown in FIG. 4A is performed according to Formula 1:

$$g(x)=1, f(x) \leq T$$
$$g(x)=0, f(x) > T \quad (1)$$

where, $f(x)$ is a pixel value at a pixel position x in the tongue image and has a range of $0 \leq f(x) \leq 255$, $g(x)$ is a pixel value indicating the inner mouth area and may be 0 or 1, and T is a threshold value which may be obtained experimentally and, for example, may be set to 70. In the meantime, at least one among Red/Green/Blue (RGB) color values of each pixel may be used as $f(x)$. Alternatively, for example, $I(x)$ corresponding to brightness in an HSI color coordinate system may be used instead of $f(x)$. In this case, in order to obtain $I(x)$ from RGB color values, RGB/HSI color coordinate system conversion formula shown in Formula 2 is used. The RGB and HSI color coordinate systems are used in this embodiment, but other various color coordinate systems such as CMY, YIQ, and HSV color coordinate systems may also be used.

$$I = F\frac{R+G+B}{3} \quad (2)$$

$$H = \frac{F}{2\pi}\cos^{-1}\left\{\frac{\frac{1}{2}[(R-G)+(R-B)]}{[(R-G)^2+(R-B)(G-B)]^{1/2}}\right\}$$

$$S = F\left\{1 - \frac{3}{R+G+B}\min(R, G, B)\right\}$$

where, $0 \leq R, G, B \leq 1$, and F is a constant, typically set to 255.

Figure 4B:
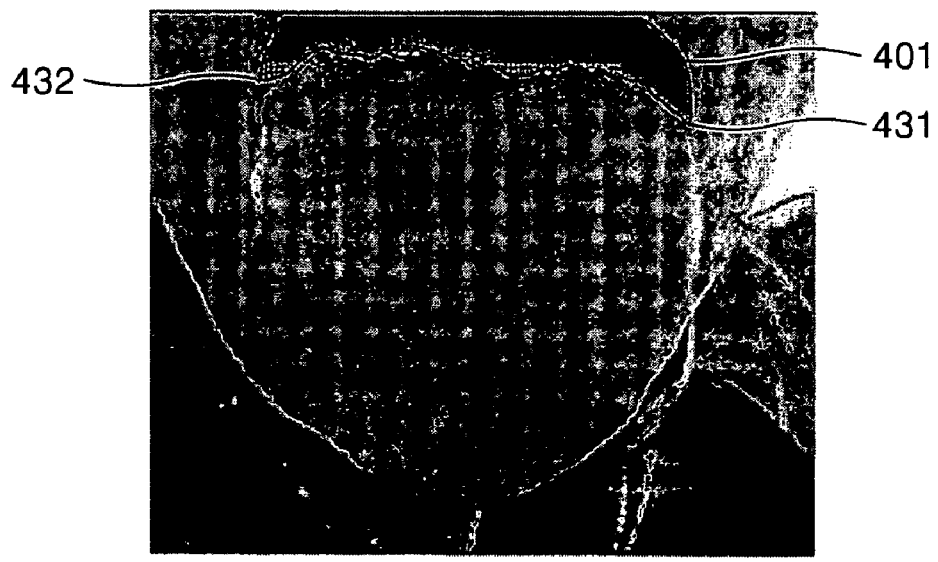
Figure 4C:
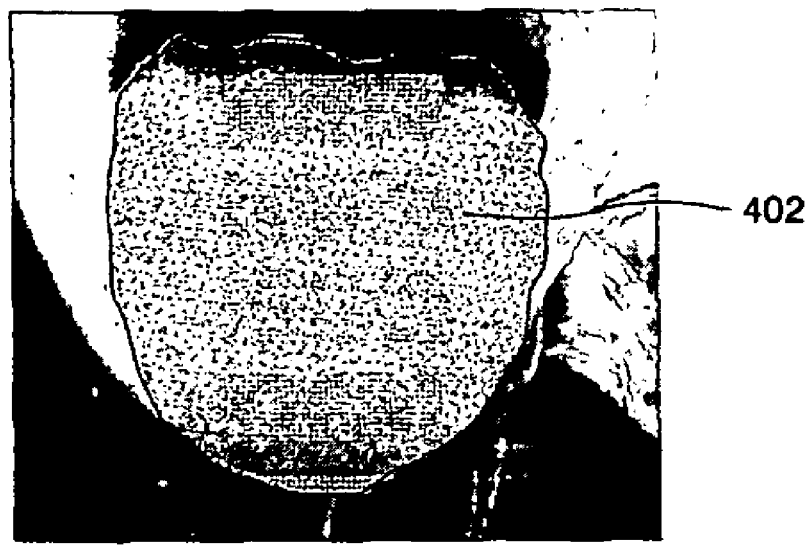

As the result of performing thresholding using Formula 1 on the tongue image shown in FIG. 4A provided from the tongue image acquisition unit 11, the tongue image is segmented into an inner mouth area 401 where $g(x)$ for each pixel is 1, as shown in FIG. 4B, and a tongue area 402 where $g(x)$ for each pixel is 0, as shown in FIG. 4C.

Figure 4D:
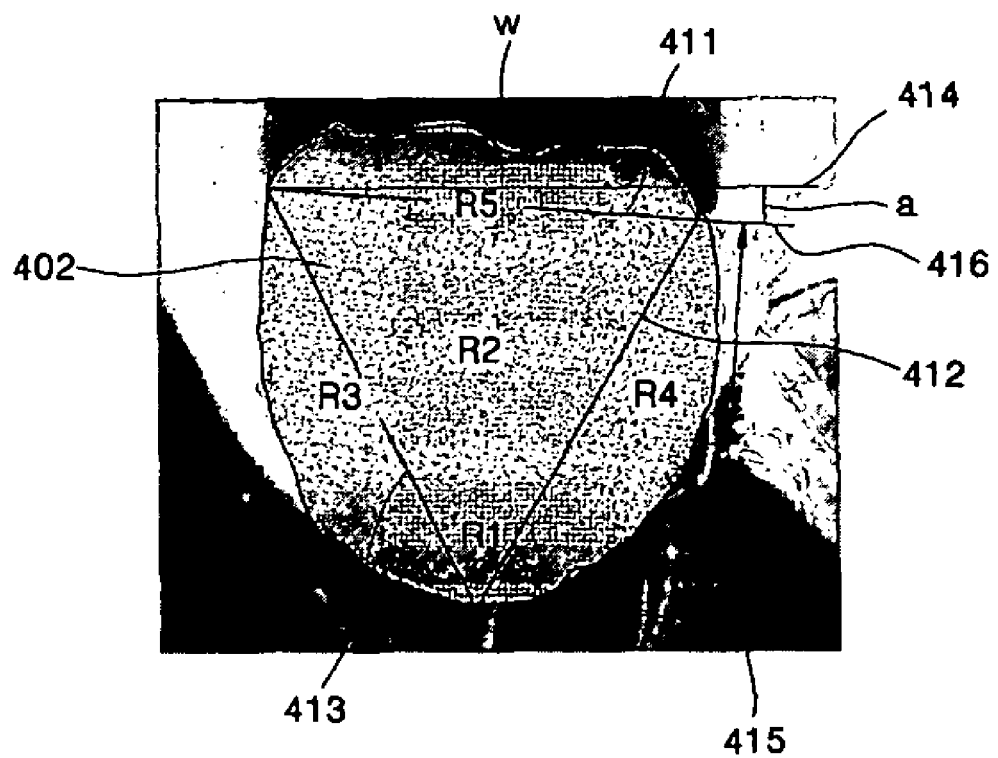
Figure 5:
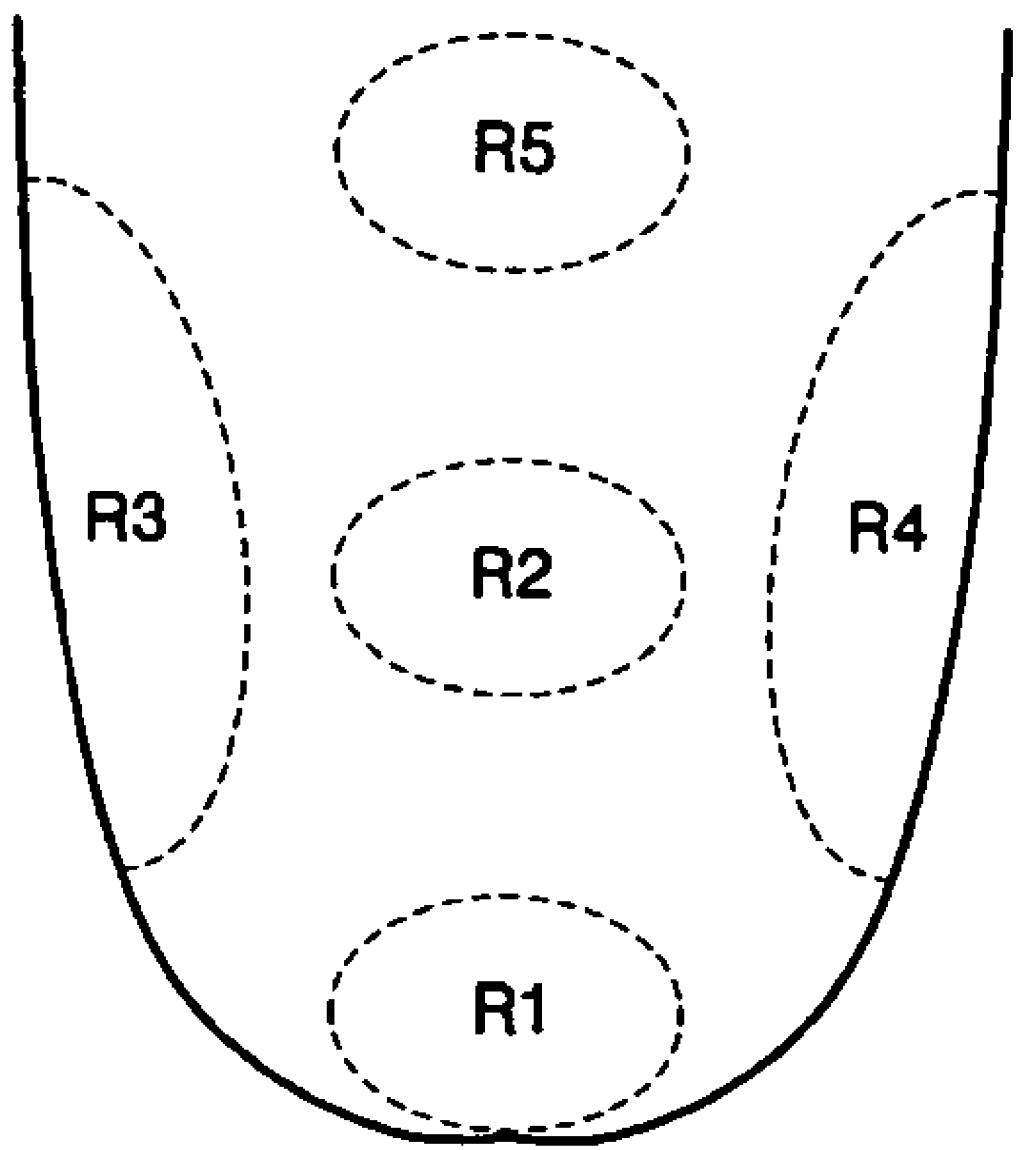
FIG. 5 illustrates a tongue showing a tip, middle part, left edge, right edge, and root of the tongue.

Next, referring to FIGS. 4B and 4D, a triangle composed of three sides 411, 412, and 413, which are defined by two opposite end points 431 and 432 of the inner mouth area 401 and a lower end point of the tongue area 402 segmented from the tongue image shown in FIG. 4A, is established. Regions of interest are set using the triangle, as shown in FIG. 5. Referring to FIG. 5, regions of interest include a tongue tip R1, a tongue middle R2, a tongue edge R3 and R4, and a tongue root R5.

In FIG. 4D, a tongue middle R2 is set to a predetermined region at a center of the tongue area 402. A tongue root R5 is set to a predetermined region at a center of the side 411. A left tongue edge R3 and a right tongue edge R4 are set to predetermined outer regions at the centers of the sides 413 and 412, respectively. A tongue tip R1 is set to a predetermined region near a point where the two sides 413 and 412 intersect.

In step 33, a tongue image is acquired from a person whose health condition is to be determined using the tongue image acquisition unit 11. Thresholding is applied to the acquired tongue image in the same manner as in the generation of the template image in step 31 to segment the acquired tongue image into the inner mouth area 401 and the tongue area 402.

In step 35, a tongue width w in the tongue area 402 is obtained based on a distance between opposite end points 431 and 432 of the inner mouth area 401, a rotation angle a of the tongue is obtained based on a horizontal line 414 starting from a left end of the side 411 and a line 416 extending from the side 411, and a tongue length l is obtained as the distance between parallel lines 415 and 416. The person's tongue image is matched with the template image using template characteristic factors, such as the tongue width w, the rotation angle a, and the tongue length l.

In step 37, regions of interest, including at least one of the tongue tip R1, the tongue middle R2, the left tongue edge R3, the right tongue edge R4, and the tongue root R5, are isolated within the acquired tongue image using the matched template image.

Hereinafter, a procedure for determining a health condition will be described with an example of a basic tongue image stored in the tongue image database 15 and an example of a tongue image currently acquired by the tongue image acquisition unit 11.

Figure 6A:
FIGS. 6A and 6B show examples of a tongue image acquired via the tongue image acquisition unit shown in FIG. 1 and a basic tongue image stored in the tongue image database shown in FIG. 1, respectively.
Figure 6B:
Figure 7A:
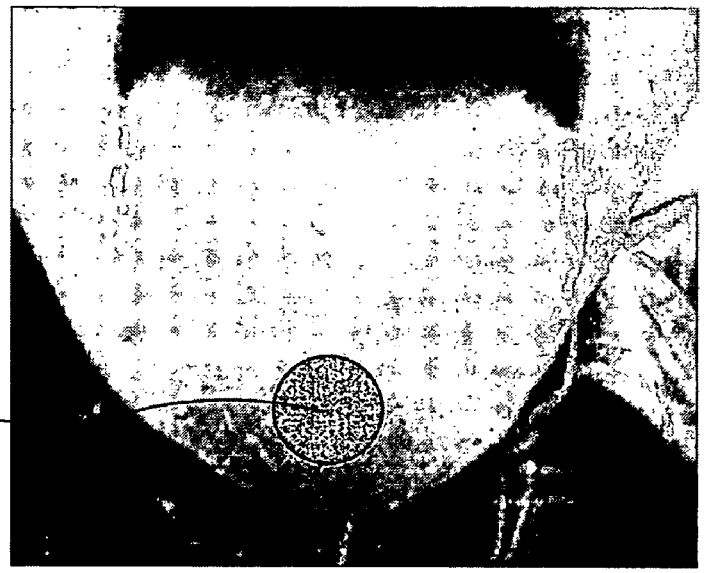
FIGS. 7A and 7B show examples of a tongue tip isolated as a region of interest from the tongue images shown in FIGS. 6A and 6B, respectively.
Figure 7B:
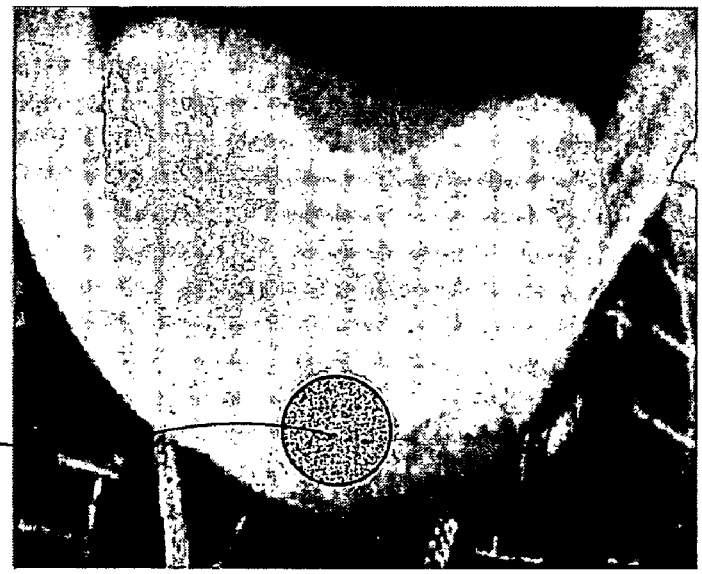
Figure 8A:
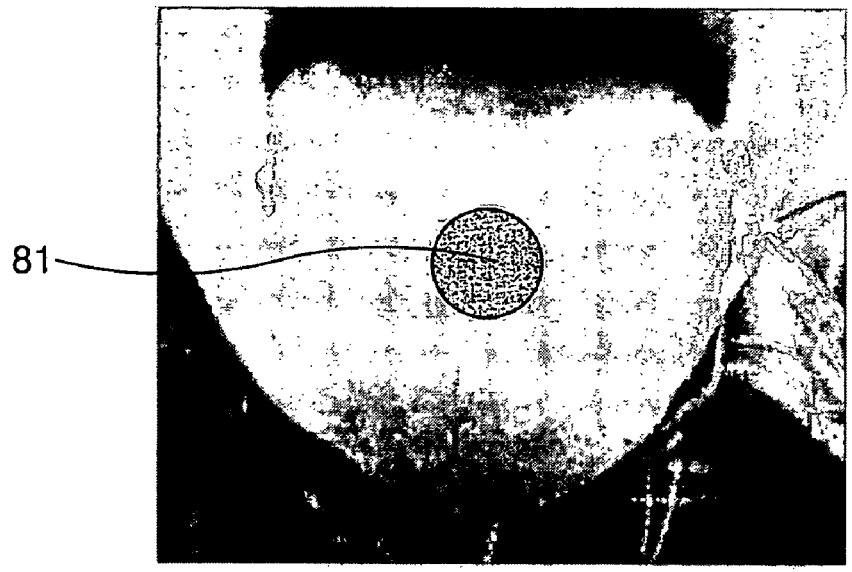
FIGS. 8A and 8B show examples of a tongue middle isolated as a region of interest from the tongue images shown in FIGS. 6A and 6B, respectively.
Figure 8B:
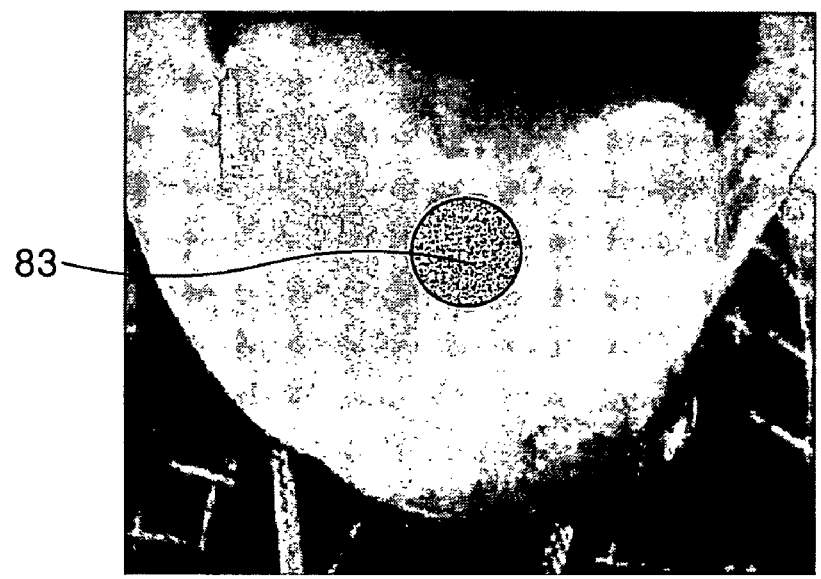

FIG. 6A is a basic tongue image stored in the tongue image database 15 corresponding to a condition of a low level of fatigue. FIG. 6B is a tongue image acquired from a person in a highly fatigued condition using the tongue image acquisition unit 11. FIGS. 7A and 7B show examples of a tongue tip isolated as a region of interest 71 from the tongue image shown in FIG. 6A and a tongue tip isolated as a region of interest 73 from the tongue image shown in FIG. 6B. FIGS. 8A and 8B show examples of respective regions of interest 81 and 83 corresponding to a tongue middle, which are isolated from the tongue images shown in FIGS. 6A and 6B, respectively.

Figure 9A:
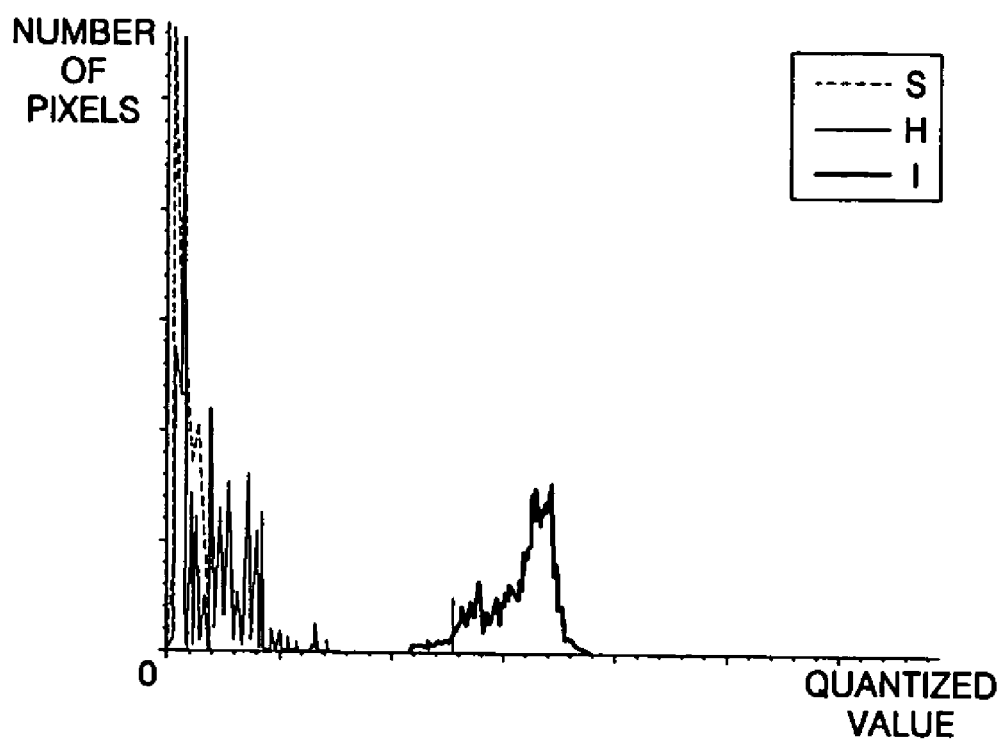
FIGS. 9A and 9B are graphs showing histograms in a Hue Saturation Intensity (HSI) color coordinate system with respect to the tongue tips shown in FIGS. 7A and 7B, respectively.
Figure 9B:
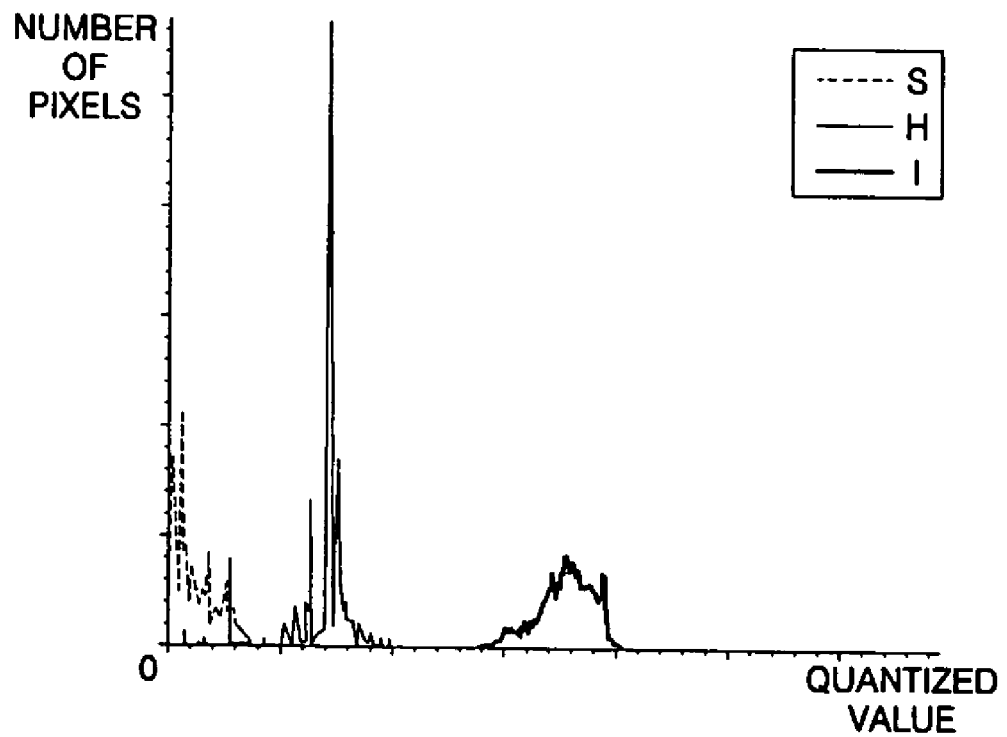
Figure 10A:
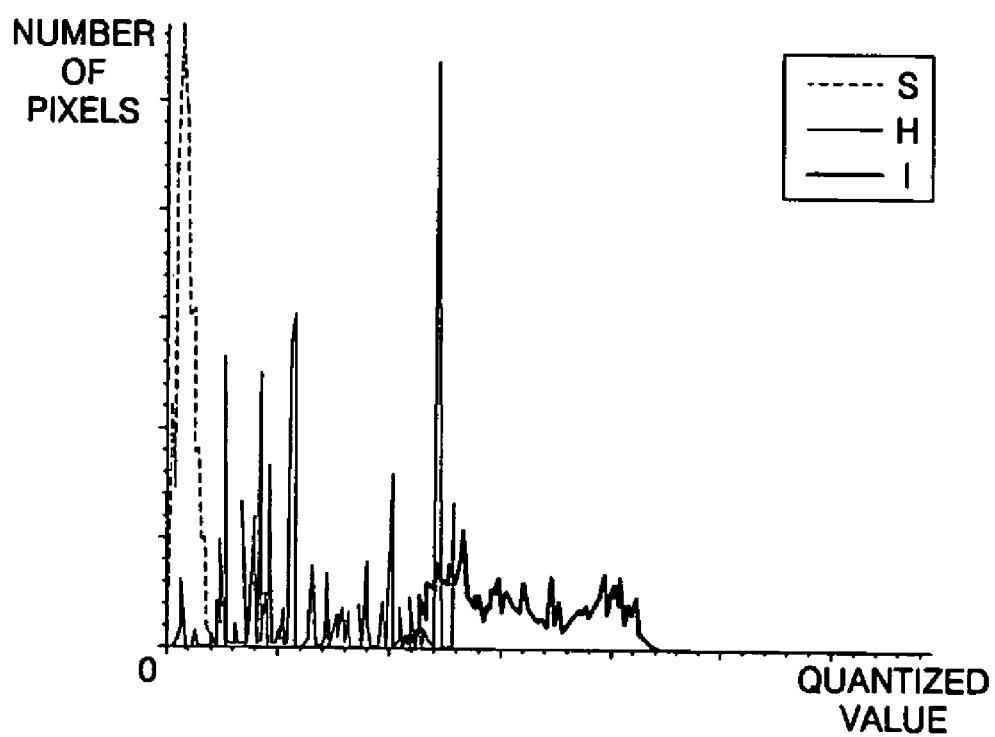
FIGS. 10A and 10B are graphs showing histograms in an HSI color coordinate system with respect to the tongue middles shown in FIGS. 8A and 8B, respectively.
Figure 10B:
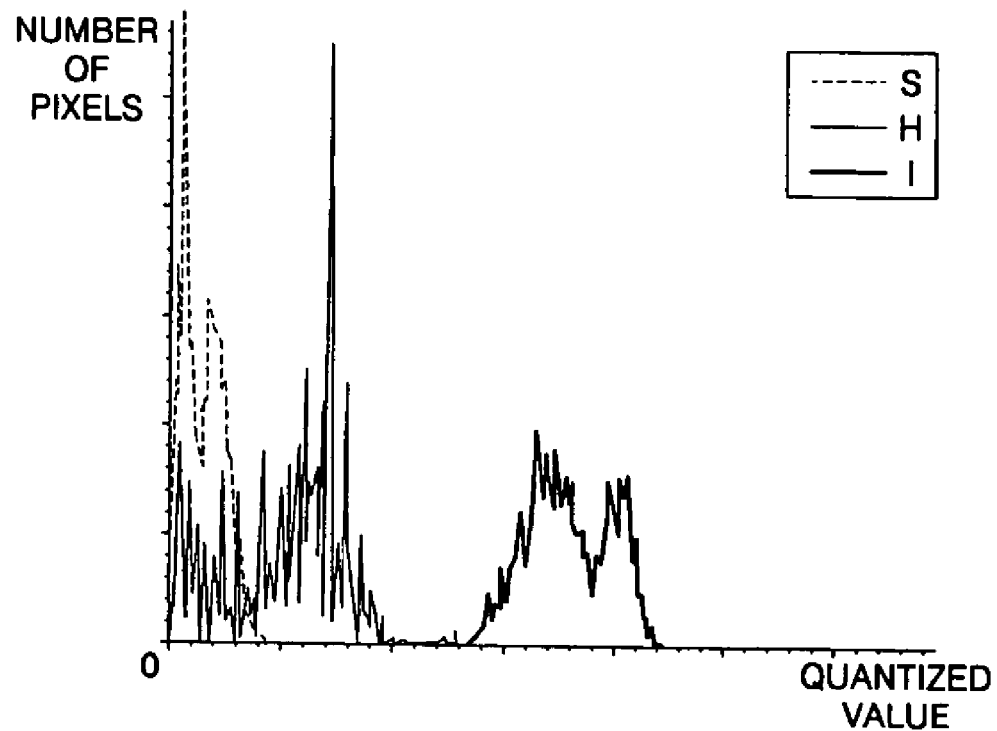

FIG. 9A shows a histogram of color values in an HSI color coordinate system with respect to the region of interest 71 corresponding to the tongue tip shown in FIG. 7A. FIG. 9B shows a histogram of color values in an HSI color coordinate system with respect to the region of interest 73 corresponding to the tongue tip shown in FIG. 7B. FIG. 10A shows a histogram of color values in an HSI color coordinate system with respect to the region of interest 81 corresponding to the tongue middle shown in FIG. 8A. FIG. 10B shows a histogram of color values in an HSI color coordinate system with respect to the region of interest 83 corresponding to the tongue middle shown in FIG. 8B.

Table 2 provides examples of characteristics of the regions of interest in the tongue images, i.e., an average ± a standard deviation with respect to each of H, S, and I, obtained from the histograms shown in FIGS. 9A through 10B.

TABLE 2

| Division | Tongue tip | Tongue middle |
|---|---|---|
| A condition of being slightly fatigue (FIG. 6A) | H = 20.23 ± 19.71<br>S = 7.51 ± 4.08<br>I = 156.64 ± 15.97 | H = 68.59 ± 14.42<br>S = 12.19 ± 9.41<br>I = 176.78 ± 12.96 |
| A condition of being very fatigued (FIG. 6B) | H = 73.26 ± 36.75<br>S = 8.38 ± 4.36<br>I = 157.55 ± 31.14 | H = 53.08 ± 25.63<br>S = 15.16 ± 8.75<br>I = 177.07 ± 18.99 |

Referring to Table 2, the H, S, and I values vary according to health conditions. In particular, the H value significantly changes depending on a health condition.

The present invention may be realized as a code that is recorded on a computer readable recording medium and may be read by a computer. For example, a method of isolating a region of interest from a tongue image may be implemented by recording on a computer readable recording medium a first program for constructing a database in which template images are stored, each template image corresponding to personal information of a person; a second program for performing thresholding using a predetermined threshold value on a tongue image, which is acquired from a person whose health condition is to be determined using a predetermined image acquisition device to segment the tongue image into an inner mouth area and a tongue area; a third program for matching the acquired tongue image with the template image using a tongue width, a rotation angle of the tongue, and a tongue length which are calculated from the tongue area; and a fourth program for isolating a region of interest, such as a tongue middle, a tongue root, a tongue edge, or a tongue tip, from the matched tongue image.

In the meantime, the computer readable recording medium may be any type of recording medium on which data that may be read by a computer system may be recorded, for example, a ROM, a RAM, a CD-ROM, a magnetic tape, a floppy disc, or an optical data storage device. The present invention may also be realized as carrier waves (for example, transmitted through Internet). Alternatively, computer readable recording media are distributed among computer systems connected through a network so that the present invention may be realized as a code that is stored in the recording media and may be read and executed in the computers. Functional programs, codes, and code segments for implementing the present invention may be easily inferred by programmers in the art of the present invention.

As described above, according to the present invention, a health monitoring apparatus using a tongue image may be implemented in a mobile communication equipment with a digital camera so that a person's health condition may be easily diagnosed based on a change in an appearance of a region of interest, such as a tongue middle, a tongue root, a tongue edge, or a tongue tip, isolated within a tongue image acquired from the person using the digital camera. Accordingly, the present invention may contribute to an advancement in personal health care.

In addition, the person's tongue image acquired using the camera may be transmitted via wires or wirelessly to a remote health care service center, in which a tongue image processing unit and a tongue image database are installed, so that a health condition may be determined through comparison of characteristic factors or may be more accurately diagnosed by an expert, such as a medical doctor with training in principles of Chinese medicine.

Moreover, the tongue image processing unit and the tongue image database may be implemented in a computer server of a mobile communication equipment company or a hospital. Thus, the company or the hospital may be effectively promoted, and provide additional, value-added services.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of monitoring health via a health monitoring apparatus using a tongue image, the method comprising:
    linking with each other a tongue image obtained from a person whose health condition is to be determined, a template image which is set for the person, and a result of determining a health condition of the person with respect to at least one characteristic factor for the person;
    storing in a database the linked tongue image, the template image and the result;
    automatically isolating a region of interest within the tongue image by using template matching with the template image of the person, which is stored in the database;
    automatically detecting at least one characteristic factor from the isolated region of interest; and
    automatically determining the health condition of the person based on a change in an appearance of the tongue in the tongue image by comparing the detected characteristic factor and a corresponding reference characteristic factor in the template image from the database.

2. The health monitoring method as claimed in claim 1, wherein isolating the region of interest comprises:
    performing thresholding on each pixel in the acquired tongue image using a predetermined threshold value to segment the tongue area from the tongue image.

3. The health monitoring method as claimed in claim 2, wherein the thresholding is performed using at least one among Red/Green/Blue (RGB) color values of each pixel in the tongue image.

4. The health monitoring method as claimed in claim 2, wherein the thresholding is performed using an intensity (I) value obtained by converting RGB color values of each pixel in the tongue image into Hue Saturation Intensity (HSI) color values.

5. The health monitoring method as claimed in claim 1, wherein the characteristic factor is an average of H, S, or I values obtained from a histogram of an HSI color coordinate system for the region of interest.

6. The health monitoring method as claimed in claim 1, wherein the region of interest is at least one region selected from the group consisting of: a tongue middle, a tongue root, a tongue edge, and a tongue tip.

7. The health monitoring method as claimed in claim 1, further comprising:
    informing the person of the result of determining the health condition via a wired connection or wirelessly.

8. A computer-readable recording medium comprising computer-executable programs recorded thereon for performing a method, execution of which by a computer facilitates health monitoring using a tongue image, the programs including:
    a first program for linking with each other a tongue image obtained from a person whose health condition is to be determined, a template image which is set for the person, and a result of determining a health condition of the person with respect to at least one characteristic factor for the person and storing in a database the linked tongue image, the template image and the result recorded on the medium;
    a second program for automatically isolating a region of interest from the tongue image using template matching recorded on the medium with the template image of the person, which is stored in the database;
    a third program for automatically detecting at least one characteristic factor from the isolated region of interest recorded on the medium; and
    a fourth program for automatically determining the health condition of the person based on a change in an appearance of the tongue in the tongue image by comparing the detected characteristic factor and a corresponding reference characteristic factor in the template image from the database.

9. A health monitoring apparatus using a tongue image, the apparatus comprising:
    a tongue image database adapted to store a tongue image obtained from a person whose health condition is to be determined, a template image which is set for the person, and a result of determining a health condition of the person with respect to at least one characteristic factor for the person,
    wherein the tongue image, the template image and the result are linked together;
    a region of interest isolator adapted to automatically isolate a region of interest within the tongue image by using template matching with the template image of the person, which is stored in the tongue image database;
    a characteristic detector adapted to automatically detect at least one characteristic factor from the isolated region of interest; and
    a health condition determiner adapted to automatically determine the health condition of the person based on a change in an appearance of the tongue in the tongue image by comparing the detected characteristic factor and a corresponding reference characteristic factor in the template image from the database.

10. The health monitoring apparatus as claimed in claim 9, further comprising:
    a color compensator for automatically compensating for color distortion of the tongue image acquired by the tongue image acquisition unit by using a color checker and for providing the compensated tongue image to the region of interest isolator.

11. The health monitoring apparatus as claimed in claim 10, wherein the color compensator generates and stores a color checker including a plurality of colors to be displayed on the tongue image during the acquisition of the tongue image, compares the color checker included in the tongue image with a color checker provided from the tongue image acquisition unit, obtains a color difference value between the two color checkers, and determines a degree of compensation based on the color difference value.

12. The health monitoring apparatus as claimed in claim 9, wherein the region of interest isolator performs template matching using a tongue width, a rotation angle of a tongue, and a tongue length, which are calculated from the tongue.

13. The health monitoring apparatus as claimed in claim 9, wherein the health monitoring apparatus is integrated into a mobile communication equipment having a digital camera.

14. The health monitoring apparatus as claimed in claim 9, wherein the health monitoring apparatus is integrated into a personal computer having a digital camera.

15. The health monitoring apparatus as claimed in claim 9, wherein the tongue image database, the region of interest isolator, the characteristic detector, the comparator, and the health condition determiner are implemented in a remote health care service center, and the tongue image acquired by the tongue image acquisition unit is transmitted via a wired connection or wirelessly to the health care service center.

16. The health monitoring apparatus as claimed in claim 15, wherein the health care service center is a computer server of a mobile communication equipment company or a hospital.

17. The health monitoring apparatus as claimed in claim 9, wherein the health condition determiner informs the person of the result of determining the health condition via a wired connection or wirelessly.

18. The health monitoring apparatus as claimed in claim 9, wherein the region of interest isolator segments the tongue area within the tongue image, by performing thresholding on each pixel in the tongue image using a predetermined threshold value to define an inner mouth area and the tongue area.

19. The health monitoring apparatus as claimed in claim 9, wherein the characteristic factor is an average of H, S, or I values obtained from a histogram of an HSI color coordinate system for the region of interest.

* * * * *